United States Patent [19]

Dery et al.

[11] Patent Number: 5,646,318

[45] Date of Patent: Jul. 8, 1997

[54] PROCESS FOR THE PREPARATION OF HYDROXYALKYLAMIDES

[75] Inventors: Maurice Dery, Putnam Valley, N.Y.; Nils Brolund, Dueren, Germany

[73] Assignee: Akzo Nobel nv, Netherlands

[21] Appl. No.: 429,337

[22] Filed: Apr. 26, 1995

[51] Int. Cl.$^6$ .................................................. C07C 231/00
[52] U.S. Cl. .................. 554/69; 554/66; 554/68; 554/70
[58] Field of Search ................ 584/66, 69, 70, 584/68

[56] References Cited

U.S. PATENT DOCUMENTS

| | | | |
|---|---|---|---|
| 2,412,113 | 12/1946 | Yauny et al. | 554/66 |
| 2,703,798 | 3/1955 | Schwartz | 554/66 |
| 2,993,887 | 7/1961 | Zech | 260/211 |

FOREIGN PATENT DOCUMENTS

| | | |
|---|---|---|
| 0473380A1 | 3/1992 | European Pat. Off. . |
| WO9206070 | 4/1992 | WIPO . |
| WO9206071 | 4/1992 | WIPO . |
| WO9206072 | 4/1992 | WIPO . |
| WO9206073 | 4/1992 | WIPO . |
| WO9206984 | 4/1992 | WIPO . |
| WO9208687 | 5/1992 | WIPO . |

*Primary Examiner*—Deborah D. Carr
*Attorney, Agent, or Firm*—Dilworth & Barrese

[57] ABSTRACT

A process is provided for producing a hydroxyalkylamide which comprises reacting alkyl ester and alkanolamine in the presence of a catalyst to provide a reaction mixture containing hydroxyalkylamide product and low boiling alcohol by-product, solidifying the hydroxyalkylamide product, neutralizing the catalyst and recovering the hydroxyalkylamide product.

29 Claims, No Drawings

PROCESS FOR THE PREPARATION OF HYDROXYALKYLAMIDES

BACKGROUND OF THE INVENTION

This invention relates to a process for the preparation of hydroxyalkylamides and, more particularly, to such a process which provides high conversion rates and low by-product formation.

A known process for producing a hydroxyalkylamide involves reacting an alkyl ester and an alkanolamine in the presence of solvent and catalyst with removal of low boiling alcohol by-product to push the reaction to completion. Besides low boiling alcohol, this process usually results in the production of one or more additional by-products, e.g., cyclic products, alkyl esters, amide esters, and the like. A typical process of this type involves reacting a fatty acid ester and an N-alkylglucamine in accordance with the reaction:

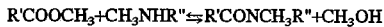

wherein R' is an alkyl group of from about 5 to about 31 carbon atoms and R" is a polyhydroxy-substituted saturated hydrocarbon group of from about 5 to about 8 carbon atoms. The fatty acid ester reactant is typically prepared by reacting an alcohol with a fatty acid. The N-alkylglucamine reactant is typically prepared by reacting an alkyl amine with a polyhydroxy reducing sugar. The hydroxyalkylamide product is recovered from the reaction mixture by stripping the solvent from the reaction mixture, e.g., by distillation. Hydroxyalkylamides can be employed as surfactants in commercial products such as laundry detergents, as detergent agents for solubilizing plasma membranes and as thickeners.

EP 473 380 discloses a method of preparing solid hydroxyalkylamides by reacting alkyl esters with alkanolamines at controlled reaction temperatures, removing the alcohol (methanol) by-product, controlling the temperature of the reaction mixture to form a thick slurry, maintaining the slurry and recovering the solid hydroxyalkylamides.

U.S. Pat. No. 2,703,798 generally relates to processes of producing various detergents wherein an aliphatic ester of a fatty acid is reacted with an N-monoalkylglucamine. Aliphatic alcohol which is liberated as a product of the reaction is removed from the reaction vessel as it is formed.

WO 92/06070, WO 92/06071, WO 92/06072 and WO 92/06073 disclose processes for manufacturing linear glucamide surfactants by reacting an N-alkylglucamine and a fatty acid ester in the presence of a catalyst.

SUMMARY OF THE INVENTION

In accordance with the present invention, a process for the production of a hydroxyalkylamide is provided wherein alkyl ester and alkanolamine are reacted in the presence of a catalyst to provide a reaction mixture containing hydroxyalkylamide, alkyl ester, alkanolamine and low boiling alcohol by-product. The reaction mixture is then cooled to a temperature which is sufficient to effect solidification of the hydroxyalkyl-amide product and the contents of the reaction mixture are held at this temperature. Conversion is continued until the reaction mixture contains appreciably little alkanolamine and alkyl ester and significant amounts of hydroxyalkylamide and low boiling alcohol by-product. The catalyst can be neutralized to lock the products of the reaction in at the desired composition. The hydroxyalkylamide product can be isolated from the reaction mixture by filtration or concentrated by distillation.

The foregoing process results in a significant increase in conversion to hydroxyalkylamide product and decrease in unreacted starting reactants compared with known processes such as those referred to above which remove low boiling by-product prior to catalyst neutralization. Another advantage of the process herein is that it can be carried out under relatively mild organic conversion reaction conditions thereby significantly reducing the formation of undesirable cyclic by-products, amide ester by-products, and the like. Moreover, the presence of low boiling by-product in the reaction mixture reduces the viscosity of the reaction mixture thereby facilitating the recovery of hydroxyalkylamide product therefrom.

DESCRIPTION OF THE PREFERRED EMBODIMENTS

The alkyl ester reactant herein is preferably derived from a saturated carboxylic or coco acid of from about 5 to about 31 carbon atoms, i.e., a fatty acid, and a saturated aliphatic alcohol of from 1 to about 6 carbon atoms and from 1 to about 6 hydroxyl groups. Preferably, said alkyl ester has the following structure:

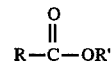

wherein R is a $C_5$-$C_{25}$ branched or straight chain alkyl or alkylene group or a substituted or unsubstituted phenyl group and R' is a $C_1$-$C_6$ substituted or unsubstituted alkyl or phenyl group. The methyl ester of stearic acid is especially preferred. Palm stearine triglyceride and similar triglycerides can also be used herein with generally good results.

The alkanolamine reactant employed herein is advantageously an N-alkyl polyhydroxy amine obtained by reacting an alkyl amine, e.g., methyl amine, with a polyhydroxy reducing sugar, e.g., glucose, fructose, maltose, lactose, galactose, mannose, xylose, sorbitol, etc., in a suitable solvent and catalytically hydrogenating the resulting product. Reactions of this type are disclosed in WO 92/06984, published Apr. 30, 1992, and WO/92/08687, published May 29, 1992, the contents of which are incorporated by reference herein.

The preferred N-alkyl polyhydroxy amine is pure white and contains no colored impurities. Also, the N-alkyl polyhydroxy amine is preferably substantially anhydrous. Suitable N-alkyl polyhydroxy amines which can be advantageously employed herein include N-methylglucamine, N-ethylglucamine, N-propylglucamine, N-butylglucamine and N-methyllactoseamine. The preferred N-alkylglucamines are derived from D-glucose, e.g., N-methyl-D-glucamine.

Industrial grade N-alkyl polyhydroxy amine can be employed herein provided certain specifications are met. Thus, industrial grade N-alkyl polyhydroxy amine may contain free sugars such as glucose, sorbitol or other relatively inert by-products in amounts of up to about 5 weight percent. However, any industrial grade N-alkyl polyhydroxy amine employed herein should have low or negligibly small amounts, e.g., no more than about 20 ppm and preferably no more than about 2 ppm, of transition metals such as nickel if the formation of color bodies or other undesirable by-products is to be minimized. It has been found that industrial grade N-alkyl polyhydroxy amines commonly contain such transition metals as a result of their manufacture by transition metal-catalyzed hydrogenation of aminated reducing sugars. One convenient check for N-alkyl polyhydroxy amine quality involves simply heating a sample of the amine to an elevated temperature, e.g., to about 140° C. N-alkyl polyhydroxy amine which quickly darkens at such a temperature is very likely to contain unacceptable levels of one or more impurities. It is usually possible to clean up industrial grade N-alkyl polyhydroxy amines which fail initial quality checks, e.g., either by washing them with methanol/water or by recrystallizing them. A useful method for lowering the level of nickel in such materials is to filter a solution of the N-alkylglucamine through basic silica gel or bleaching earth.

The alkyl ester and alkanolamine can be reacted in the presence of solvent and transesterification catalyst. Suitable solvents include hydroxy solvents such as methanol, ethanol, propanol, isopropanol, butanol, glycerol, 1,2-propylene glycol, 1-3-propylene glycol, and the like. Methanol is a preferred monohydroxy solvent and 1,2-propylene glycol is a preferred dihydroxy solvent. Mixtures of solvents can also be employed herein.

Catalysts which can be employed herein are not particularly limited and can be selected from among the alkoxides, hydroxides, carbonates, phosphates, pyrophosphates, polyphosphates, tartrates, citrates, silicates, aluminosilicates, and the like. Preferred alkoxide catalysts include the alkali metal $C_1$-$C_4$ alkoxides such as sodium methoxide, potassium ethoxide, etc. The alkoxide catalysts can be prepared separately from the reaction mixture, or can be generated in situ using an alkali metal such as sodium. For in situ generation, e.g., sodium metal in a methanol solvent, it is preferred that the other reactants not be present until catalyst generation is complete.

Other catalysts suitable for use herein include trilithium phosphate, trisodium phosphate, tripotassium phosphate, tetrasodium pyrophosphate, tetrapotassium pyrophosphate, pentasodium tripolyphosphate, pentapotassium tripolyphosphate, lithium carbonate, sodium carbonate, potassium carbonate, disodium tartrate, dipotassium tartrate, sodium potassium tartrate, trisodium citrate, tripotassium citrate, sodium basic silicates, potassium basic silicates, sodium basic aluminosilicates, potassium basic silicates, sodium basic aluminosilicates, potassium basic aluminosilicates and mixtures thereof. Potassium carbonate has provided particularly good results. The catalyst typically is used at levels of from about 0.1 to about 50, preferably from about 0.5 to about 20, more preferably from about 5 to about 15, mole percent of the N-alkyl polyhydroxy starting reactant. Mixtures of catalysts can also be used.

The alkyl ester and alkanolamine may mix with some difficulty. This is especially true when the alkyl ester is relatively hydrophobic, e.g., in the case of the ethyl ester of a $C_{16}$ or higher saturated fatty acid or triglyceride. To solve this problem, a nonionic surfactant can be employed as a phase transfer agent or emulsifier as disclosed in WO 92/06071, published Apr. 16, 1992, the contents of which are incorporated herein by reference. When a phase transfer agent is utilized in the instant process, it is employed at a level of from about 0.5 to about 95 weight percent of the reaction mixture, excluding catalyst. High levels such as 50 weight percent or more are best reserved to those processes where reaction times can be kept very short, e.g., in continuous processes. In a batch (i.e., noncontinuous) process, a preferred level is from about 0.5 to about 20 weight percent, more preferably from about 1 to about 20 weight percent, most preferably from about 1 to about 10 weight percent of the reaction mixture, excluding catalyst. Such levels are also suitable for use in continuous processes. Continuous processes, will, of course, concurrently recycle some catalyst.

Generally, phase transfer agents include the nonionic surfactants. Preferably, phase transfer agents are selected from the polyethylene oxide condensates of alkylphenols, the condensation products of aliphatic alcohols and ethylene oxide, the condensation products of ethylene oxide and a hydrophobic base derived from the condensation of propylene oxide and propylene glycol, the condensation products of ethylene oxide and the product resulting from the reaction of propylene oxide and ethylenediamine and the alkyl polysaccharides. More preferably, phase transfer agents include saturated fatty alcohol polyethoxylates, alkylpolyglycosides, linear glucamides, mixtures thereof, and the like.

The organic conversion reaction conditions, i.e., temperature, pressure, time and proportions of starting reactants, utilized herein can be as follows. Temperatures in the present process will generally not exceed 100° C. and preferably will range from about 25° to about 80° C. and more preferably from about 65° to about 75° C. Pressures utilized in the process herein are atmospheric. Main reaction time, i.e., the time required for the alkyl ester and alkanolamine to completely react, can range from about 0 to about 12 hours, preferably from about 60 to about 360 minutes.

Alkyl ester and alkanolamine are employed as starting reactants in this process in approximately equimolar proportions in terms of the number of moles of fatty carbonyl moieties of the alkyl ester per mole of alkanolamine. A slight molar excess of alkyl ester, e.g., about 1.10 moles per mole of alkanolamine, can be employed with advantageous results. A slight molar excess of alkanolamine can also be employed.

In contrast to the prior art processes referred to above, the hydroxyalkylamide produced in accordance with the present invention is solidified prior to recovery by cooling the reaction mixture containing the hydroxyalkylamide and low boiling alcohol by-product to a temperature which will result in crystallization of at least a major amount of the hydroxyalkylamide product ("main fraction"). It has been found that when the reaction mixture is cooled to a temperature less than about 45° C., crystallization of the hydroxyalkylamide product will generally occur. It is generally preferred to cool the reaction mixture to a temperature less than about 35° C., i.e., to about room temperature. Generally, the reaction mixture should be cooled for a time which can range from about 0.5 hours to about 48 hours. Preferably, the reaction mixture is cooled for a time which can range from about 1 to about 36 hours and more preferably from about 6 to about 15 hours. Thereafter, the catalyst can be neutralized to lock the products of the reaction in at the desired composition.

In one embodiment of the present invention, the crystallized main fraction is recovered from the reaction medium. Recovery of the main fraction can be carried out by any suitable technique, e.g., filtration. No attempt is made in this embodiment to remove any low boiling by-product from the reaction mixture. It may be advantageous to repeat the crystallization step to reclaim additional quantities of hydroxyalkylamide product not initially recovered as the main fraction. Thus, the mother liquor remaining after recovery of the main fraction is again cooled to a suitable temperature to crystallize hydroxyalkylamide product remaining therein ("minor fraction"). The crystallized minor fraction is recovered as before, e.g., by filtration, to provide additional hydroxyalkylamide product. Alternatively, the mother liquor can be recycled back into subsequent batches.

In a second embodiment for recovering hydroxyalkylamide product, which is preferred in the practice of this invention, the solidified hydroxyalkylamide product is formulated into an aqueous solution which is convenient for handling and non-flammable. This can be accomplished by adding a sufficient quantity of water to the reaction mixture to formulate the hydroxyalkylamide product into an aqueous solution. The low boiling alcohol by-product can then be removed by any suitable technique, e.g., distillation, to thereby recover hydroxyalkylamide. It is important to neutralize the catalyst before reheating the reaction mixture when distilling low boiling alcohol by-product. If the reaction mixture is reheated before neutralizing the catalyst, the reaction will revert back to the starting materials resulting in a significant loss of yield.

While removal of low boiling alcohol by-product from the reaction mixture can be carried out in the presence or absence of water, it is preferred to have water present so that the resultant product will be fluid and easily handled. Foaming problems are not encountered during the distillation of alcohol in the presence of water. Distillation can be carried out at pressures ranging from about 1 atm to about 0.1 mm Hg, with pressures of about 1 atm being preferred. Some water may distill with the low boiling alcohol and it may be necessary to add water over the course of the distillation.

The choice of neutralizing agent depends on the catalyst used. Generally, the neutralizing agent can be selected from the group of weakly acidic compounds, for example, citric acid, acetic acid, carbonic acid, mixtures thereof, and the like. Citric acid is the preferred neutralizing agent.

Hydroxyalkylamide produced by the reaction of alkyl ester and alkanolamine in accordance with the present invention will correspond to the general formula $R^1CONR^2R^3$ wherein $R^1$ is the alkyl moiety of the alkyl ester, $R^2$ is the alkyl moiety of the alkanolamine and $R^3$ is the polyhydroxy-substituted saturated hydrocarbon group of the alkanolamine. Typically, $R^1$ is a $C_5$-$C_{31}$ alkyl moiety, preferably $C_7$-$C_{19}$ alkyl, most preferably straight chain $C_{11}$-$C_{19}$ alkyl, or mixture thereof. Typically, $R^2$ is $C_1$-$C_6$ alkyl, 2-hydroxyethyl, 2-hydroxypropyl, or mixture thereof, preferably $C_1$-$C_4$ alkyl, more preferably $C_1$ or $C_2$ alkyl, most preferably $C_1$ alkyl. Typically, $R^3$ is a polyhydroxy-substituted hydrocarbon group derived from a reducing sugar such as glucose, fructose, maltose, lactose, galactose, mannose, xylose, high dextrose corn syrup, high fructose corn syrup and high maltose corn syrup. Preferably, $R^3$ is selected from among —$CH_2$—$(CHOH)_n$—$CH_2OH$, —$CH(CH_2OH)$—$(CHOH)_{n-1}$—$CH_2OH$, —$CH_2(CHOH)_2(CHOR^4)(CHOH)$—$CH_2OH$, where n is an integer from 3 to 5 and $R^4$ is H or a cyclic mono- or poly-saccharide and alkoxylated derivatives thereof. More preferably, $R^3$ is —$CH_2$—$(CHOH)_4$—$CH_2OH$. The hydroxyalkylamide produced in accordance with this invention can be provided in the form of premixes with co-surfactants, solutions or solid crystals.

COMPARATIVE EXAMPLES 1-3

The following comparative examples illustrate the prior art method of producing hydroxyalkylamide wherein low boiling by-product, specifically, methanol, is removed from the reaction mixture prior to removing the hydroxyalkylamide product.

Hardened palm stearine triglyceride (MOFAC 1660; Source: Akzo Pacific Oleo Chemicals; 140.8 g; 0.168 moles; MW 838 g/mol) was melted and dissolved in methanol (48 g) to provide a MOFAC 1660 solution. Then, N-methylglucamine (NMGA; Source Rhône-Poulenc; (97.5 g; 0.5 mol; 195 g/mol) and NaOCH₃ as catalyst (Comparative Example 1; 2.25 g), Na₂CO₃ as catalyst (Comparative Example 2; 1.73 g) and Na₂CO₃ as catalyst (Comparative Example 3; 1.33 g) were individually admixed with the MOFAC 1660 solution while stirring vigorously to provide three reaction mixtures. Thereafter, the three reaction mixtures were heated until stable reflux of methanol was achieved at a temperature ranging from about 73° to about 75° C.

All reaction mixtures became clear solutions after 3.5 to 6.5 hours depending on the catalyst used. The net reaction time allowed to complete conversion ranged from 6 to 8 hours until removal of methanol commenced.

Methanol was removed by gentle distillation at ambient pressure. In order to maintain distillation of the methanol, the temperature was incremented stepwise until a final temperature of 130° C. was reached. At the same time vacuum was cautiously pulled to prevent formation of an extremely stable foam. Considerable attention was required to prevent the reaction mixtures from entering parts of the distillation equipment. The whole vacuum gradient procedure took about 90 minutes. Finally, the vacuum was set to 45 mbar and allowed to last for the next 90 minutes in order to complete removal of volatiles. Then the GA product was cooled to room temperature and ground to powder.

The GA product was subjected to analysis for NMGA, total GA and soap by titration; linear and cyclic GA were determined by HPLC. Results are set forth in Table I below.

EXAMPLE 1

This example illustrates the process of this invention wherein hydroxylalkylamide product is removed from the reaction mixture without removing low boiling by-product.

The process was carried out as follows: hardened palm stearine triglyceride (MOFAC 1660; Source: Akzo Pacific Oleo Chemicals; 140.8 g; 0.168 moles; MW 838 g/mol) was melted and dissolved in methanol (156.6 g). Then, N-methylglucamine (NMGA; Source: Rhône-Poulenc; 97.5 g; 0.5 mol; 195 g/mol) and K₂CO₃ as catalyst (2.25 g; 10 mol percent based on NMGA) were admixed with the MOFAC 1660 solution while stirring vigorously. The reagents were brought to reaction by slurrying up in methanol at 60 weight percent solids. At no time the temperature exceeded 70° C. In the work up part of the reaction, GA product was recovered by crystallization in accordance with the present invention instead of by distillative methanol removal as in Comparative Examples 1-3.

In the initial period of the reaction the reaction mixture turned pasty but remained well agitable. The slurry was gently heated until stable reflux of methanol was achieved at 70° C. Occasionally, the mixture slightly foamed in the next 15 minutes. After 45 minutes most of the NMGA solids were reacted and the reaction mixture became translucent. During the next 45 minutes, all solids disappeared and the reaction mixture became clear. Then the reaction was allowed to complete conversion to linear GA during the next 210 minutes. Overall, 300 minutes since onset of reflux were spent for the main reaction time.

For work up, the reaction mixture was allowed to cool to room temperature and crystallize overnight. Crystals ("main fraction") were removed on a φ 5 cm SEITZ filter press and washed twice with methanol at 6.5% of the wet filter cake mass. The wet GA cake was dried in open air to a constant weight. Thus, 217 g of powder GA with no detectable cyclic GA present were obtained as the main fraction. The combined mother liquors were then cooled to 5° C. and again crystallized over night at 5° C. ("minor fraction"). The solids were removed, washed and dried as described above. 8.4 g of powder GA were recovered from the mother liquors with no detectable cyclic GA having been formed. The final mother liquors were evaporated in a rotavap until dryness and 13.5 g of a wax-like material was obtained as residue for disposal.

The major and minor GA fractions were subjected to analysis for NMGA, total GA and soap by titration; linear GA and cyclic GA were determined by HPLC. Results are set forth in Table I below.

TABLE I

| | Temp. Main Rxn., °C. | Residual NMGA, (wt %) | GA Titrat., (wt %) | Linear GA, HPLC, (wt %) | Cyclic GA, HPLC, (wt %) |
|---|---|---|---|---|---|
| Comparative Example 1 | 75 | 3.4 | 84.3 | 81.1 | 1.8 |
| Comparative Example 2 | 75 | 3.7 | 82.9 | 77.5 | 3.8 |
| Comparative Example 3 | 75 | 3.4 | 82.9 | 77.5 | 4.1 |
| Example 1 Main GA Fraction | 70 | 1.0 | 92.7 | 94.2 | 0 |
| Example 1 Minor GA Fraction | 70 | 1.0 | 88.6 | 87.5 | 0 |

As can be clearly seen from the data presented in Table I, the amount of residual NMGA produced in the main fraction and minor fraction of Example 1 (1.0 wt %) was considerably lower relative to the amounts of residual NMGA for Comparative Examples 1-3 (3.4, 3.7 and 3.4 wt. %, respectively) while the amounts of linear GA, i.e., hydroxyalkylamide product, produced in the main fraction and minor fraction of Example 1 (94.2 and 87.5 wt %, respectively) were significantly higher than the amounts of linear GA produced in Comparative Examples 1-3 (81.1., 77.5 and 77.5 wt %, respectively). Furthermore, it can be seen that the reaction of Example 1 was carried out at a lower temperature, i.e., at 70° C., which prevented the formation of cyclic GA.

While the invention has been particularly shown and described with reference to various embodiments, it will be recognized by those skilled in the art that modifications and changes may be made to the present invention without departing from the spirit and scope thereof, which is set forth in the following claims.

COMPARATIVE EXAMPLE 4

The following comparative example illustrates the prior art method of producing hydroxyalkylamide wherein the low boiling by-product, specifically, methanol, is removed from the reaction mixture prior to neutralizing the catalyst. The product is then formulated as an aqueous solution suitable for use in detergent formulations.

n-Methyl glucamine (NMGA; Source: Aldrich Chemicals; 73.7 g) and propylene glycol (Source: Aldrich Chemicals; 15.4 g) were heated and stirred together until a homogeneous solution was obtained. Sodium methoxide solution (Source: Aldrich Chemicals, 6.1 g) and fatty acid methyl ester (Source: Procter & Gamble CE 1270, 86.3 g) were charged and the reaction mixture held between 90° and 100° C. for 1 hour. Some of the reaction mixture was removed (56.7 g) and used for the preparation of Example 2 below. Methanol was removed by vacuum distillation. Enough water was added to produce a solution with a final solids level of approximately 50%. The pH was adjusted with citric acid to between 6 and 7.

EXAMPLE 2

A sample of the reaction mixture, as prepared above in Comparative Example 4, was allowed to cool to room temperature over night. Water (30.2 g) and citric acid (0.4 g) were added and the resultant slurry was mixed and heated to 88° C. Methanol was collected as it distilled. The solids of the final solution were adjusted with water to approximately 50% and the pH was checked to be between 6 and 7.

Comparative results between the two methods are given in the table below. The results in the table were normalized to a solids level of 51.5%.

| Analysis | Comparative Example 4 | Example 2 |
|---|---|---|
| hydroxylalkylamide product | 44.9% | 49.0% |
| fatty acid | 2.80% | 0.51% |
| amide ester | 0.76% | 0.36% |
| NMGA | 3.13% | 0.30% |
| cyclic by-product | 520 ppm | 209 ppm |

As can be seen from these data, the process of this invention resulted in a significant increase in the production of hydroxylalkylamide product (i.e., linear GA) relative to the known prior art process exemplified in Comparative Example 4. Furthermore, a significant decrease in cyclic by-product was obtained relative to Comparative Example 4. These data clearly demonstrate the superiority of the instant invention over known prior art processes for producing hydroxyalkylamides.

What is claimed is:

1. A process for producing a hydroxyalkylamide which comprises reacting alkyl ester and alkanolamine to provide a reaction mixture containing hydroxyalkylamide product, low boiling by-product and unreacted alkyl ester and alkanolamine and thereafter cooling the reaction mixture to solidify hydroxyalkylamide product and shift the reaction equilibrium to the production of additional hydroxyalkylamide product and low boiling by-product accompanied by a reduction in the amounts of unreacted alkyl ester and alkanolamine, the process being conducted without removing any appreciable amount of low boiling by-product from the reaction mixture.

2. The process of claim 1 carried out in the presence of solvent.

3. The process of claim 1 carried out in the presence of catalyst and, following the production of additional hydroxyalkylamide product, catalyst activity is terminated to substantially prevent reversion of hydroxyalkylamide product to alkyl ester and alkanolamine.

4. The process of claim 3 wherein the catalyst is selected from the group consisting of the alkoxides, hydroxides, carbonates, phosphates, pyrophosphates, polyphosphates, tartrates, citrates, silicates, aluminosilicates and mixtures thereof.

5. The process of claim 1 wherein hydroxyalkylamide product is solidified by cooling the reaction mixture to a temperature less than about 45° C.

6. The process of claim 1 wherein hydroxyalkylamide product is solidified by cooling the reaction mixture to a temperature less than about 35° C.

7. The process of claim 1 wherein the alkyl ester is derived from a fatty acid and an alcohol.

8. The process of claim 7 wherein the fatty acid is a $C_5$-$C_{25}$ fatty acid and the alcohol is a $C_1$-$C_6$ alcohol.

9. The process of claim 1 wherein said alkyl ester is of the formula:

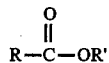

wherein R is a $C_5$-$C_{25}$ straight or branched chain alkyl or alkylene group or a substituted or unsubstituted phenyl group and R' is a $C_1$-$C_6$ substituted or unsubstituted alkyl or phenyl group.

10. The process of claim 1 wherein the alkyl ester is selected from the group consisting of monoglyceride, diglyceride and triglyceride.

11. The process of claim 1 wherein the alkanolamine is the hydrogenated product of the reaction of an alkyl amine and a reducing sugar.

12. The process of claim 1 wherein the alkanolamine is selected from the group consisting of N-methylglucamine, N-methyl-D-glucamine, N-methyllactoseamine, N-ethylglucamine, N-propylglucamine and N-butylglucamine.

13. The process of claim 1 wherein the alkyl ester is a triglyceride and the alkanolamine is the hydrogenated product of the reaction of an alkyl amine and a reducing sugar.

14. The process of claim 1 wherein the alkyl ester is a triglyceride and the alkanolamine is selected form the group consisting of N-methylglucamine, N-methyl-D-glucamine, N-methyllactoseamine, N-ethylglucamine, N-propylglucamine and N-butylglucamine.

15. The process of claim 1 wherein the alkyl ester and alkanolamine are reacted in the presence of catalyst.

16. The process of claim 2 wherein the solvent is selected from the group consisting of methanol, ethanol, propanol, isopropanol, butanol, glycerol, 1,2-propylene glycol, 1-3-propylene glycol and mixtures thereof.

17. The process of claim 15 wherein the catalyst is selected from the group consisting of the alkoxides, hydroxides, carbonates, phosphates, pyrophosphates, polyphosphates, tartrates, citrates, silicates, aluminosilicates and mixtures thereof.

18. The process of claim 1 further comprising reacting alkyl ester and alkanolamine in the presence of phase transfer agent.

19. The process of claim 18 wherein the phase transfer agent is selected from the group consisting of nonionic surfactants, saturated fatty alcohol polyethoxylates and alkyl polyglycosides.

20. A process for producing a hydroxyalkylamide which comprises reacting an alkyl ester derived from a $C_5$-$C_{25}$ fatty acid and a $C_1$-$C_6$ alcohol with an alkanolamine which is the hydrogenated product of the reaction of an alkyl amine and a reducing sugar in an inert solvent in the presence of catalyst to provide a reaction mixture containing hydroxyalkylamide product, low boiling alcohol by-product and unreacted alkyl ester and alkanolamine and thereafter cooling the reaction mixture to solidify hydroxyalkylamide product and shift the reaction equilibrium to the production of additional hydroxyalkylamide product and low boiling alcohol by-product accompanied by a reduction in the amounts of unreacted alkyl ester and alkanolamine, the process being conducted without removing any appreciable amount of low boiling alcohol by-product from the reaction mixture.

21. The process of claim 20 wherein the solvent is selected from the group consisting of methanol, ethanol, propanol, isopropanol, butanol, glycerol, 1,2-propylene glycol, 1-3-propylene glycol and mixtures thereof and the catalyst is selected from the group consisting of the alkoxides, hydroxides, carbonates, phosphates, pyrophosphates, polyphosphates, tartrates, citrates, silicates, aluminosilicates and mixtures thereof.

22. The process of claim 20 wherein the alkyl ester and alkanolamine are reacted at a temperature which avoids the production of any significant quantity of cyclic hydroxyalkylamide by-product.

23. The process of claim 22 wherein the temperature does not exceed about 70° C.

24. The process of claim 20 wherein the hydroxyalkylamide product is solidified by cooling the reaction mixture to a temperature less than about 35° C.

25. The process of claim 20 wherein the hydroxyalkylamide product is solidified by cooling the reaction mixture to a temperature less than about 45° C.

26. The process of claim 21 wherein following the production of additional hydroxyalkylamide product, catalyst activity is terminated to substantially prevent reversion of hydroxyalkylamide product to alkyl ester and alkanolamine and low boiling alcohol by-product is removed from the reaction mixture.

27. The process of claim 26 wherein prior to removing the low boiling alcohol by-product, water is added to the reaction mixture in an amount sufficient to formulate the hydroxyalkylamide product into an aqueous solution.

28. The process of claim 26 wherein catalyst activity is terminated by contacting the catalyst with a weakly acidic compound.

29. The process of claim 28 wherein the weakly acidic compound is selected from the group consisting of citric acid, acetic acid, carbonic acid and mixtures thereof.

* * * * *